United States Patent [19]

Nakaoji

[11] 3,988,344

[45] Oct. 26, 1976

[54] PROCESS FOR PURIFYING SACCHARIN
[75] Inventor: Kozo Nakaoji, Osaka, Japan
[73] Assignee: Daiwa Kasei Kabushiki Kaisha, Osaka, Japan
[22] Filed: June 10, 1975
[21] Appl. No.: 585,761

[52] U.S. Cl.................................. 260/301; 426/429; 426/548
[51] Int. Cl.²......................................... C07D 275/06
[58] Field of Search ............ 426/429, 548; 260/301

[56] References Cited
FOREIGN PATENTS OR APPLICATIONS
6,065    3/1902    United Kingdom................. 260/301
21,417   11/1893   United Kingdom................. 260/301

OTHER PUBLICATIONS
Abstract—"Removing o- and p-toluenesulfonamide and p-sulfamoylbenzoic acid from Saccharin", 54:15319h, 1959.
Abstract—"Impurities in Saccharin and Bladder Cancer", 79:62421c, 1973.
Abstract—"A Rapid Method for the Estimation of Impurities in Saccharin and Sodium Saccharin", 66:22256c.

Primary Examiner—Frank W. Lutter
Assistant Examiner—N. Greenblum
Attorney, Agent, or Firm—Larson, Taylor and Hinds

[57] ABSTRACT

A process for purifying saccharin comprising the steps of adding butyl acetate or a mixture of butyl acetate and ethyl acetate as an extracting solvent to an aqueous solution of water-soluble metal salt or ammonium salt of saccharin to remove organic impurities from the saccharin by extraction, the volume of ethyl acetate not exceeding that of butyl acetate, concentrating and cooling the resulting aqueous layer to precipitate crystals having an organic impurity content of not higher than 120 p.p.m. and recrystallizing the crystals from water to obtain saccharin having an organic impurity content of not higher than 10 p.p.m.

6 Claims, No Drawings

PROCESS FOR PURIFYING SACCHARIN

This invention relates to a process for purifying saccharin by removing organic impurities therefrom.

Presently, various investigations are being made on the possible harmfulness of saccharin, an artificial sweetener, to the human body. Reportedly, the harmfulness of saccharin has recently been found to be attributable mainly to organic impurities contained therein rather than to saccharin itself.

The impurities contained in saccharin differ depending on the method by which it is produced. When it is prepared by the oxidation of o-toluenesulfonamide, impurities include unreacted o-toluenesulfonamide, p-toluene-sulfonamide present in small amounts in the starting material and p-sulfamoylbenzoic acid which results from the oxidation of p-toluenesulfonamide, etc. Further whatever method is employed, saccharin contains impurities such as o-sulfamoylbenzoic acid derived from the decomposition of saccharin itself during the manufacturing step thereof and ammonium o-sulfonylbenzoate produced when the acid is further hydrolyzed. Among these impurities, p-toluene-sulfonamide is contained o-toluenesulfonamide, presently used as the starting material, in a relatively small amount of about 10 p.p.m. This toluene sulfonamide is removed during production, so that the saccharin obtained is almost free from this substance. The impurities that are contained in relatively larger amounts are o-toluenesulfonamide and o-sulfamoylbenzoic acid.

Usually, saccharin is prepared by oxidizing o-toluenesulfonamide followed by centrifuging and washing with water to obtain crude saccharin, neutralizing and thereafter filtering the crude product with a caustic alkali, concentrating the filtrate under reduced pressure to precipitate crystals and recrystallizing the crystals from water. The saccharin prepared by this method usually contains 50 to 100 p.p.m. of organic impurities. Although the organic impurities when present in such amounts were in no way considered to be objectionable, recent investigations have shown that they produce an adverse effect on the human body.

The object of this invention is to provide a process for purifying saccharin by removing organic impurities to obtain purified saccharin having an impurity content of no higher then 10 p.p.m.

Other objects and features of this invention will become apparent from the following description.

In order to achieve the foregoing objects, the first inventor conducted various investigations on recrystallization using water. Consequently, the conventional recrystallization process was found infeasible on an industrial scale because the recrystallization procedure must be repeated at least three times to achieve purification to the above-mentioned level, with a new mother liquor produced each time which must be further treated.

Accordingly, directing attention to the fact that, although saccharin itself is sparingly soluble in water, water-soluble metal salts or ammonium salts of saccharin are readily soluble in water whilst the organic impurities contained in saccharin are insoluble in water, the inventor made a concentrated effort to find solvents in which water-soluble metal salts or ammonium salts of saccharin are insoluble but organic impurities are readily soluble and which are hardly miscible with water. As a result, it has been found that butyl acetate or a mixture of butyl acetate and ethyl acetate achieves the object of this invention. More specifically, it has been found that removal of the organic impurities from aqueous solution of saccharin salt by extraction with the abovementioned solvent, followed by concentration and subsequent cooling of the resulting aqueous phase, gives saccharin crystals having an impurity content no higher than 120 p.p.m. and that the impurity content can be reduced to a remarkably low level of up to 10 p.p.m. by a single procedure of recrystallizing the crystals from water. Based on these findings this invention has been accomplished.

The process for purifying saccharin of this invention comprises the steps of adding butyl acetate or a mixture of butyl acetate and ethyl acetate to an aqueous solution of water-soluble metal salt or ammonium salt of saccharin to remove organic impurities from the saccharin by extraction, concentrating and cooling the resulting aqueous layer to precipitate crystals having an organic impurity content of not higher than 120 p.p.m. and recrystallizing the crystals from water to obtain saccharin having an organic impurity content of not higher than 10 p.p.m.

According to this invention, it is critical to use butyl acetate singly or a mixture of butyl acetate and ethyl acetate as an extraction solvent, whereby organic impurities can be effectively extracted, making it possible to obtain saccharin crystals having an organic impurity content of up to 120 p.p.m. by subsequently concentrating and cooling the resulting aqueous layer. Use of ethyl acetate renders the process more economical due to its lower cost compared with that of butyl acetate, but the volume of ethyl acetate must not exceed that of butyl acetate. If the volume of ethyl acetate in the mixture is larger or when ethyl acetate alone is used, the solvent fails to achieve effective extraction of impurities and is not serviceable as intended, because ethyl acetate and water are considerably soluble in each other. In contrast, butyl acetate has a sufficient ability to dissolve impurities, is almost insoluble in water, has a relatively high boiling point, is readily recoverable and is therefore superior in safety and economy when recovering the extraction solvent for example by distillation.

With this invention, water-soluble metal salts or ammonium salts of crude saccharin are used. These salts are prepared, for example, by oxidation of o-toluene sulfonamide using potassium dichromate as a catalyst, followed by neutralizing the oxidants with at least one basic compound selected from the group consisting of hydroxides and carbonates of alkali metals, hydroxides and carbonates of alkaline earth metals, ferrous hydroxide, ferric hydroxide and ammonia. More specific examples of these salts are sodium, potassium, calcium, iron and ammonium salts of saccharin. Among these salts, sodium salt is usually preferred in view of existing pharmacopoeial standards and regulations for food additives. In the above neutralization step, usually, the oxidants are added to an aqueous solution of the above basic compounds and the mixture is stirred maintaining the solution at a pH of 7 to 10 at room temperature to 40° C.

The present process will be described below in detail. An extraction solvent is added to an aqueous solution of saccharin salt for extraction. Prior to this extraction, an aqueous solution of saccharin salts obtained by the above neutralization is preferably filtered to remove insolubles such as dust and then the filtrate is adjusted to a pH of 4 to 7 with dilute mineral acid such as hydrochloric acid. With this acidification of the filtrate, part of the impurities precipitate which can be easily removed by decantation. In the extraction, predominant amounts of impurities, especially o- or p-toluenesulfonamide, o-sulfamoylbenzoic acid and like organic impurities are transferred into the solvent, whereas the saccharin salt remains unextracted. When allowed to stand for some time, the mixture separates into a solvent layer and an aqueous solution layer. Concentration of the aqueous solution of saccharin salt used above is usually 20 to 50% by weight. The amount of the extraction solvent is suitably determined in accordance with the amount of impurities contained in the salt of saccharin. The extraction is usually conducted in a vessel equipped with a stirrer and a countercurrent condenser at a temperature of about 20° to 50° C for about 1 to 5 hours. After the extraction is completed, the mixture is transferred into a separating apparatus and then allowed to stand for 0.5 to 2 hours. Then the solvent layer is removed, and the aqueous layer is concentrated under reduced pressure of about 20 to 70 mm Hg to remove part of water and then left for standing at room temperature to give crystals of saccharin salt, which are filtered off. The crystals will be hereinafter referred to as "primary crystals." Since the mother liquor resulting from the filtration contains a considerable amount of unprecipitated saccharin salt, it is preferable to reuse the mother liquor in the next cycle of solvent extraction for the removal of impurities from crude saccharin. Further preferably, the solvent layer separated in the extraction step is distilled to recover the extraction solvent for reuse.

The primary crystals filtered off must have a reduced organic impurity content of not higher than 120 p.p.m. The primary crystals are then recrystallized from water to obtain crystals having a further reduced organic impurity content of not higher then 10 p.p.m. The crystals will be hereinafter referred to "secondary crystals." The recrystallization to obtain the secondary crystals is usually carried out in the following manner. The primary crystals obtained by the aforementioned method are dissolved in water at a temperature of about 40° to 70° C to obtain an aqueous solution of saccharin salt having a concentration of about 50 to 70% by weight, and then the solution is allowed to stand and cool. Then the purified saccharin crystals precipitate. If the impurity content of the primary crystals is above 120 p.p.m., it is impossible for a single recrystallization procedure to reduce the impurity content to a level not higher than 10 p.p.m. For the recrystallization of the primary crystals to afford the secondary crystals, the mother liquor separated from the secondary crystals by filtration is usuable in place of water. For this purpose, the mother liquor is preferably subjected to solvent extraction before it is used for recrystallization, so as to remove accumulated organic impurities which would lower the purity of the secondary crystals to be formed. When followed as stated in Example 3, this procedure is industrially advantageous because the recrystallization step gives purified saccharin in improved yields.

For a better understanding of this invention examples are given below.

EXAMPLE 1

Crude saccharin (800 g) obtained by oxidation of o-toluenesulfonamide and containing the impurities of about 5,000 p.p.m. is placed in a 2-liter beaker and neutralized to a pH of 8.0 with 1,700 g of 30% aqueous solution of sodium hydroxide while maintaining the contents at a temperature of up to 40° C with cooling. The solution is filtered to remove chrominum hydroxide derived from the oxidation step of o-toluenesulfonamide and other insolubles such as dust, sand, etc. and the filtrate is adjusted to a pH of 6 with dilute hydrochloric acid, by which part of impurities precipitates. One liter of supernatant of the filtrate is placed into a 2-liter three-necked flask equipped with a stirrer and a countercurrent condenser, 1000 cc of butyl acetate is added to the filtrate, and the mixture is stirred at room temperature for 2 hours to effect full extraction and then transferred into a separating funnel. When allowed to stand for one hour, the mixture separates into an aqueous solution layer and an organic layer. The aqueous layer is separated off, placed into a branched flask and concentrated at a reduced pressure of 20 mm Hg to remove about 360 cc of water, whereupon concentration is discontinued. The concentrate is placed into a beaker, left at room temperature with stirring for crystallization, and filtered to obtain 180 g of primary crystals.

The primary crystals are dissolved in 70 cc of distilled water with stirring and heating to 60° C. The solution is left to cool with stirring to precipitate secondary crystals, which are filtered off, washed with water and dried.

Results:

|  | Amount (g) | Impurity content (p.p.m.) |
|---|---|---|
| Primary crystals | 180 | 70 |
| Secondary crystals | 90 | 2 |

EXAMPLE 2

In the same manner as in Example 1, crude saccharin is neutralized with 30% aqueous solution of sodium hydroxide and then filtered to obtain a filtrate. A mixture of 400 cc of butyl acetate and 400 cc of ethyl acetate is added to one liter of the filtrate to precipitate crystals, following the same procedure as in Example 1.

Results:

|  | Amount (g) | Impurity content (p.p.m.) |
|---|---|---|
| Primary crystals | 210 | 100 |
| Secondary crystals | 109 | 5 |

EXAMPLE 3

Butyl acetate (100 cc) is added to 120 cc of the mother liquor obtained by filtering off the secondary crystals in Example 1 and the same extraction procedure as in Example 1 is repeated to prepare an aqueous solution (about 120 cc). Primary crystals (160 g) prepared by the same extraction procedure as in Example 1 are added to the aqueous solution, the mixture is heated to 65° C with stirring and the resulting solution is left to cool to yield secondary crystals.

Results:

| Secondary crystals | Amount (g) | Impurity content (p.p.m.) |
|---|---|---|
| | 100 | 6 |

What I claim is:

1. A process for purifying saccharin comprising the steps of adding an extracting solvent selected from the group consisting of butyl acetate and a mixture of butyl acetate and ethyl acetate, where the volume of ethyl acetate does not exceed that of butyl acetate, to an aqueous solution of water-soluble metal salt or ammonium salt of saccharin to remove organic impurities from the saccharin by extraction, separating the resulting aqueous layer from the organic layer, concentrating and cooling the resulting separated aqueous layer to precipitate crystals having an organic impurity content of not higher then 120 p.p.m., dissolving the precipitated crystals in water and recrystallizing the crystals from the water to obtain saccharin having an organic impurity content of not higher then 10 p.p.m.

2. The process as defined in claim 1 wherein said extracting solvent is butyl acetate.

3. The process as defined in claim 1 wherein said extracting solvent is a mixture of butyl acetate and ethyl acetate, the volume of ethyl acetate not exceeding that of butyl acetate.

4. The process as defined in claim 1 wherein said water-soluble metal salt of saccharin is a salt selected from the group consisting of alkali metal, alkaline earth metal and iron salts of saccharin.

5. The process as defined in claim 1 wherein said extraction is conducted at a temperature in the range of about 20° to 50° C.

6. The process as defined in claim 1 wherein said concentration of aqueous layer is carried out under reduced pressure of about 20 to 70 mm Hg.

* * * * *